United States Patent [19]

Byrne

[11] Patent Number: 5,403,295
[45] Date of Patent: Apr. 4, 1995

[54] MEDICAL DEVICES HAVING AN ELECTRICALLY CONDUCTIVE HYDROGEL COATING

[75] Inventor: Phillip O. Byrne, Whickham, England

[73] Assignee: British Technology Group Ltd., London, England

[21] Appl. No.: 137,192

[22] PCT Filed: May 13, 1992

[86] PCT No.: PCT/GB92/00858
§ 371 Date: Oct. 26, 1993
§ 102(e) Date: Oct. 26, 1993

[87] PCT Pub. No.: WO92/20396
PCT Pub. Date: Nov. 26, 1992

[30] Foreign Application Priority Data

May 13, 1991 [GB] United Kingdom .................. 9110334

[51] Int. Cl.⁶ .......................................... A61M 31/00
[52] U.S. Cl. .................................................... 604/265
[58] Field of Search ................ 604/264, 265, 280, 20, 604/53, 266; 128/640, 798

[56] References Cited

U.S. PATENT DOCUMENTS

| | | | |
|---|---|---|---|
| 4,569,673 | 2/1986 | Tasi | 604/20 |
| 4,674,512 | 6/1987 | Rolf | 128/640 |
| 5,205,297 | 4/1993 | Montecallo et al. | 128/798 |

FOREIGN PATENT DOCUMENTS

| | | |
|---|---|---|
| 0323711 | 7/1989 | European Pat. Off. . |
| 0365138 | 4/1990 | European Pat. Off. . |
| 2219510 | 12/1989 | United Kingdom . |

Primary Examiner—John D. Yasko
Assistant Examiner—Manuel Mendez
Attorney, Agent, or Firm—Nixon & Vanderhye

[57] ABSTRACT

A medical device, such as a catheter (10), for location at least partially within a patient's body for a period of at least the order of a day, includes an electrode (11) connected in an electrical circuit (11,12,13) operable to generate by way of the electrode an electric field to inhibit bacterial attachment and colonization on and adjacent to the device/body interface, and the electrode includes an electrically conductive hydrogel coating (11) to define the device/body interface. The coating can be loaded with a salt to ensure conductivity and pH material to stabilize the surrounding hydrogen ion concentration in use of the device.

8 Claims, 1 Drawing Sheet

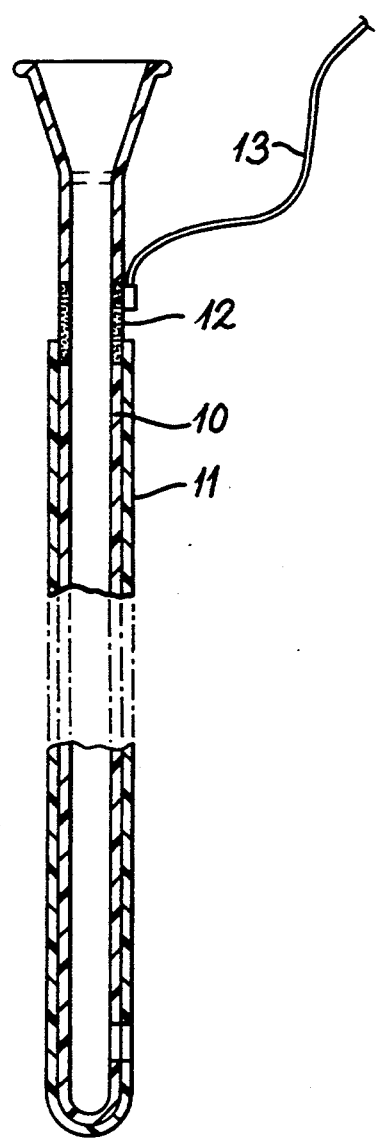

MEDICAL DEVICES HAVING AN ELECTRICALLY CONDUCTIVE HYDROGEL COATING

This invention concerns medical devices and more particularly such devices according to Patent Specification GB 2,219,510A.

BACKGROUND OF THE INVENTION

These last devices are for location at least partially within a patient's body for a period of at least the order of a day and comprise means operable to generate an electric field acting, in use of the device, to inhibit bacterial attachment and colonisation on and adjacent to the device/body interface. In one device form the generating means comprise an electrode for or in connection with an electrical circuit, the electrode being supported by the device and the circuit being operable to generate the appropriate field by way of the electrode.

DESCRIPTION OF THE INVENTION

According to the present invention the conductor in the last form of device comprises an electrically conductive hydrogel coating which itself serves to define the interface with the body during use of the device.

An advantage of the invention is that the subject devices may benefit in other ways from the application of a hydrogel coating. For example, catheters can be provided with such a coating to facilitate insertion in a patient by the reduction of frictional forces.

In order to ensure conductivity, with substantially predictable electrical properties, the hydrogel will be loaded with a salt, such as sodium or potassium chloride, or other appropriate material. Clearly this material should be compatible with both the patient's body and the hydrogel in the sense that it should give rise to no undesirable consequences.

Preferably, in addition, the hydrogel is loaded with material to regulate the pH level round the device. This pH buffer will stabilise the hydrogen ion concentration around the device when current is flowing in use.

The loading of material to ensure conductivity and provide a pH buffer can, of course, be effected in preparation of the hydrogel for application to the device during manufacture. However, insofar as the device may be made available to a user in a dehydrated form, which is to be rehydrated as a preliminary to use, loading can alternatively be effected by solution of the relevant material in the rehydration liquid. The invention accordingly also contemplates the provision of a device with a hydrogel coating in association with appropriate loading material and, correspondingly, the preparation of a device by the provision of a suitably loaded hydrogel coating.

BRIEF DESCRIPTION OF THE DRAWINGS

The invention is illustrated by way of example in the accompanying drawing which shows in schematic cross-section a device of tubular form, such as a catheter 10, having over its end portion for insertion in a patient a hydrogel coating 11.

As indicated above the coating is loaded with material to ensure conductivity and provide a pH buffer. Also, in order to ensure reliable connection with an associated electrical circuit, the catheter is provided with a terminal electrode 12 which is engaged by the coating and has a lead 13 connected therewith. The electrode 12 is suitably of annular form circumscribing the catheter towards its extracorporeal end, the electrode itself comprising a carbon-loaded zone of the plastics material from which the catheter is made or being of other suitable construction, and being at least partially superimposed by the coating in electrically conductive engagement.

I claim:

1. A medical device for location partially within a patient's body for a period of at least the order of a day, said device comprising an electrode connectable with an electrical circuit operable to generate by way of said electrode an electric field acting in use of the device to inhibit bacterial attachment and colonization on and adjacent to the device/body interface, said electrode comprising a hydrogel coating to define said interface, said hydrogel coating being loaded with a salt to ensure conductivity with substantially predictable electrical properties, said hydrogel coating being dehydrated prior to use and requiring rehydration as a preliminary to use.

2. A device according to claim 1, wherein said electrode is connected to a said electrical circuit.

3. A device according to claim 1, which is made of a plastics material.

4. A device according to claim 1, wherein said hydrogel coating is loaded with pH buffer material to stabilize the hydrogen concentration around said coating during use.

5. A device according to claim 1 in the form of a catheter or like tubular device having said hydrogel coating around an end portion thereof intended for location in a patient.

6. A device according to claim 5 and including circumferentially partway therealong an annular terminal electrode having an elongate electrical connector lead extending therefrom, said annular electrode being at least partially superimposed by said hydrogel coating in electrically conductive engagement therewith.

7. A combination comprising a device according to claim 1 and separate material for incorporation into said device by way of an associated rehydration liquid for said hydrogel coating, said separate material including at least one of a salt to ensure conductivity with substantially predictable electrical properties for said hydrogel coating and a pH buffer for stabilizing the hydrogen ion concentration around said hydrogel coating during use.

8. A combination according to claim 7, wherein said salt is selected from the group consisting of sodium chloride and potassium chloride.

* * * * *